United States Patent [19]

Kleinfeld

[11] Patent Number: 5,470,714

[45] Date of Patent: Nov. 28, 1995

[54] ONE-STEP FREE FATTY ACID DETERMINATION METHOD

[75] Inventor: Alan M. Kleinfeld, La Jolla, Calif.

[73] Assignee: Lidak Pharmaceuticals, La Jolle, Calif.

[21] Appl. No.: 157,965

[22] Filed: Nov. 24, 1993

Related U.S. Application Data

[63] Continuation-in-part of Ser. No. 827,057, Oct. 28, 1992, abandoned, which is a continuation-in-part of Ser. No. 624,125, Dec. 7, 1990, abandoned, which is a continuation-in-part of Ser. No. 449,972, Dec. 12, 1989, abandoned.

[51] Int. Cl.$^6$ ................................................ G01N 33/533
[52] U.S. Cl. .................. 435/7.8; 435/968; 436/518; 436/815
[58] Field of Search .................... 435/7.8, 968; 436/518, 436/815

[56] References Cited

PUBLICATIONS

Richieri et al., A Fluorescently Labeled Intestinal Fatty Acid Binding Protein. Interactions with Fatty Acids and Its Use in Monitoring Free Fatty Acids. Journal of Biological Chemistry 267(33):23495–23501, 1992.

*Primary Examiner*—Toni R. Scheiner
*Assistant Examiner*—Donna C. Wortman
*Attorney, Agent, or Firm*—Knobbe, Martens, Olson & Bear

[57] ABSTRACT

A one reaction step method for determining hydrophobic analytes, such as free hydrophobic analytes, comprising the steps of mixing a solution suspected of containing the hydrophobic analyte, e.g. free fatty acid, with a reagent comprising a fluorescently modified specific-binding protein for the hydrophobic analyte, detecting a fluorescence difference between the fluorescently modified specific-binding protein in the bound and unbound condition, and relating said fluorescence difference to the amount of arialyre in the solution is disclosed.

3 Claims, 7 Drawing Sheets

ONE-STEP FREE FATTY ACID DETERMINATION METHOD

This is a continuation-in-part of U.S. patent application No. 07/827,057, filed Oct. 28, 1992, now abandoned, which in turn is a continuation-in-part of U.S. patent application No. 07/624,125, filed Dec. 07,1990, now abandoned, which in turn is a continuation-in-part of U.S. patent application No. 07/449,972, filed Dec. 12, 1989, now abandoned, to which priority is claimed.

BACKGROUND OF THE INVENTION

This invention relates to biochemical assays for a wide class of free fatty acids, retinol and wherein the analyte is caused to react with a specific binding fluorescently modified, small molecular weight protein, and thereby causes a detectable fluorescence signal. A one-step assay for free fatty acids, either in whole blood, serum, food preparations, or various laboratory conditions using a suitably altered fatty-acid-binding protein (FABP) is provided. To date, fourteen different probes for detecting and measuring free fatty acids have been constructed using the principles taught hereinafter.

Long chain free fatty acids (FFA) with acyl chains> 16 carbons are quantitatively the most important physiological energy source. While ubiquitous and essential for normal physiological function, FFA are also potent modulators of cellular activity, Karnovsky, M. J., Kleinfeld, A. M., Hoover, R. L. and Klausner, R. D. J. Cell Biol. 49:1–6, 1982; Richieri, G. and Kleinfeld, A. M., J. Immunol. 145:1024–1077, 1990. There are, in fact, numerous indications that FFA levels uniquely reflect various states of health and disease. Variations in total fatty acid (FA) levels have been reported in a number of pathologies including AIDS, ischemia, inflammation, diabetes, immune dysfunction, and cancer. Brown, R. E., Steele, R. W., Marmer, D. J., Hudson, J. L. and Brewster, M. A. J. Immunol. 131:1011, 1983; Hochachka, P.W. Science 231:234, 1986; Levy, J.A. in Basic and Clinical Immunology, D. P. Stites. J. D. Stobo, H. H. Fudenberg, and J. V. Wells, eds., Lange Medical Publications, Los Altos, CA, pp. 293–301, 1984; Reaven, G. M., Hollenbeck, C. Jeng, C. Y, Wu, M. S. and Chen, Y-D.I. Diabetes 7:1020, 1988; Tsuchiya, H., Hayashi, T., Sato, M., Tatsumi, M. and Takagi, N. J. Chromatogr. 309:43, 1984.

In specific instances, the concentration of FFA may be of significant importance in the diagnosis or treatment of disease or in studying the underlying biochemical or immunochemical causes or effects of disease. For example: FFA are believed to be important factors in the cause of ventricular arrhythmias during acute myocardial infarction, Makiguchi M, Hokkaido Igaku Zasshi (JAPAN) Jul 1988, 63 (4) p 624–34. Significant differences in free fatty acids from normal levels in AIDS patients may be implicated in the pathophysiology of AIDS and could represent a good index of diagnosis and prognosis, Christeff, N.; Michon, C.; Goertz, G.; Hassid, J.; Matheron, S.; Girard, P.M.; Coulaud, J. P.; Nunez, E. A. et. al., EUR. J. CANCER CLIN. ONCOL.; 24(7), pp. 1179–1183 1988. Ambient plasma free fatty acid concentrations in non-insulin-dependent diabetes mellitus may be indicative of insulin resistance, Fraze, E.; Donner, C. C.; Swislocki, A.L.M.; Chiou, Y.-A.M.; Chen, Y.-D.I.; Reaven, G. M., J. CLIN. ENDOCRINOL. METAB.; 61(5), pp. 807–811 1985. Fatty acids have been implicated in the pathogenesis of thromboatherosclerosis, Tavella, M.; Mercuri, 0.; de Tomas, M.E., NUTR. RES.; 5(4), pp. 355–365 1985. Depression of serum calcium may result from increased plasma free fatty acids, Warshaw, A. L.; Lee, K.-H.; Napier, T. W.; Fournier, P. O.; Duchainey, D.; Axelrod, L., GASTROENTEROLOGY; 89(4), pp. 814–820 1985.

Elevated levels of FA have been found in human cancer patients and murine models (Ligaspi, A., Jeevanandam, M., Starnes, H. F., & Brennan, M. F., Metabolism 36:958, 1987; Iguchi, T., Takasugi, N., Nishimura, N., & Kusunoki, S. Cancer Res. 49:821, 1989; Brown, R. E., Steele, R. W., Marmer, D. J., Hudson, J. L., & Brewster, M. A. J. Immunol. 131:1001, 1983) and these elevated levels were shown to result in immunological deficiencies (Brown, R. E., Steele, R. W., Marmer, D. J., Hudson, J. L., & Brewster, M. A. J. Immunol. 131:1001,1983).

In addition to their importance in disease, the measurement of FFA levels has important applications in a wide variety of biochemical, biophysical, cell biologic, and physiological research. These include studies of FFA transport (Storch, J. and Kleinfeld, A.M., Biochemistry 25:1717, 1986; Potter, B. J., Sorrentino, D. and Berk, P. D., Ann. Rev. Nutr. 9:253, 1989), inter and intra-cellular signalling (Kim, D., Lewis, D. L., Graziadel, L., Heer, E. J., Bar-Sagi, D. and Clapham, D. E., Nature 337:557, 1989), and membrane structural perturbation (Karnovsky, M. J., Kleinfeld, A. M., Hoover, R. L., and Klausher, R. D. J. Cell Biol. 49:1, 1982.) The study of Storch et. al., in which the present inventor was a major participant, was designed to use special (synthetic-fluorescent) FFA to probe the structure of the protein, not to determine the aqueous phase concentration of FFA. The technique described by Storch et. al. cannot be used to measure the concentration of natural FFA. FFA found in serum (natural FFA) have-no fluorescent or any other groups that can be used for detection so the only way to detect them is to make the protein fluorescent. In this invention, it is the protein that is fluorescent, as it must be for the present method to work: Storch et. al. measured the binding to the fatty binding protein of synthetic (fluorescent) FA that have an anthracene group covalently attached through an ester linkage (the AOFFA). Storch et. al. did not determine the aqueous phase (or even protein bound) concentration of these AOFFA because they could not. The method that storch et. al. employed does not allow quantitation of the AOFFA bound to the protein. To do this would require a determination of the absolute quantum yield of the AOFFA within the protein binding site and this was not done. The fluorescence of the AOFFA does not shift when AOFFA moves from water to protein. In other words there is only one wavelength (band) of emission whether there is binding or not. The shift in wavelength that the present inventor discovered and discloses herein occurs for the probes in the present invention. It is this shift in emission wavelength that is particularly important to quantitation of the absolute FFA concentration and which is important in the invention described in this patent.

While vital information about both normal and pathological physiology would accrue from the measurement of plasma levels of FFA, there have been two essential barriers to obtaining this information. First, no method has previous existed for measuring the aqueous phase concentration of unbound FA (FFA). Direct measurements of FFA have I 0 not been possible previously because their low aqueous phase solubility causes long chain FA to adhere to virtually all surfaces and therefore monomer concentrations, in aqueous solutions, cannot be determined by physical separation. The un-esterified and unbound (as opposed to bound to serum albumin) FFA in the aqueous phase is, however, the active form of the FA in both normal and pathologic states.

Second, although the concentration of unbound FFA can be estimated, this can be done only with considerable effort. The unbound FFA concentration is estimated from the ratio of total serum FA to total serum albumin. Once the total FA and total albumin have been measured, the unbound FFA concentration is calculated using the FA-albumin association coefficients (~8 different sites/albumin molecule) determined from measurements of FFA partition between an albumin-water phase and heptane, Ashbrook, J. D., Spector, A. A., Santos, E. C. and Fletcher, J. E. J. Biol. Chem. 250:2233, 1975, Richieri, G. V., Anel, A., and Kleinfeld, A. M., Biochemistry 32; 7574, 1993. Typical values calculated in this fashion yield concentrations in the range of 2 to 200 nM. Even this estimate, however, can only be obtained with considerable effort since the determination of both total FA and total albumin concentrations requires several very time-consuming and expensive steps.

Determination of total FA and albumin first requires the separation of plasma and cellular components in whole blood. This is done by centrifugation and decantation of the upper (plasma) phase. A colorimetric or ELISA assay can be used for determining the plasma concentration of albumin. Several approaches have been used to determine total FA. In the most common, the lipid fraction must first be extracted from total plasma using, essentially, the method of Folch et. al., Folch, J., Lees, M. and Stanley, G. H. S. J. Biol. Chem. 226:497, 1957. This method involves suspension of a quantity of plasma fluid in a solution of chloroform:methanol, centrifugation of this mixture and decantation of the supernatant, re-extraction of the residue with methanol:chloroform:water, centrifugation of this second mixture followed by decantation of the second supernatant and combination with the first. Chloroform is added to the combined supernatants, a twophase mixture is produced by centrifugation, and the lower chloroform phase which contains the lipid is saved. At this stage most previous workers have concentrated the chloroform phase, derivatized the fatty acids to methyl esters and then performed chromatography to quantirate the various components. Baty, J. D. and Pazouki, S. J. Chromat. 395:403, 1987. It is possible, however, to determine the total FA content of a heptane extract by adding a chloroform solution containing a divalent cation such as 63Ni to the heptane extract. A two phase system is produced in which the upper phase contains complexes (probably micelies) of 63Ni complexed with the anionic FFA and the total FFA concentration can be determined from the 63Ni activity, Ho, R.J. Anal. Blochem. 36: 105, 1970. A variation on these approaches involves the direct derivatization of FA while in plasma, using visible-UV FFA reactive reagents (Miwa, H., Yamamoto, M., Nishida, T., Nunoi, K. and Kikuchi, M. J. Chromat. 416:237, 1987. The derivatized FFA complex is then extracted from plasma using organic solvents and FFA are then assayed using HPLC.

Another method for estimating lipid component is described by Imamura Shigeyuki, et. al., U.S. Pat. No. 4,491,631, wherein an enzyme having enoyl-coA hydratase activity, 3-hydroxyacyl-coA dehydrogenase activity and 3-ketoacyl-coA thiolase activity, all in the same enzyme, is produced by culturing the microorganism strain Pseudomonas fragi b-0771 FERM-p no. 5701, and isolating the enzyme thus produced from the culture medium. The enzyme is useful in an assay method for a fatty acid component in a sample, which fatty acid is originally present in the sample or is liberated from a fatty acid ester in the sample. The assay is carried out by converting the fatty acid to acyl-coA, converting the thus-produced acyl-coA to dehydroacyl-coA; converting the thus-produced dehydroacyl-coA to hydroxyacyl-coA, converting the thus-produced hydroxyacyl-coA to ketoacyl-coA, converting the thus-produced ketoacyl-coA to acyl-coA and measuring the detectable changes in the reaction mixture.

These assay methods generally are complicated and time consuming, and are not readily carried out in any but a well-equipped research laboratory. Moreover they are determinations of the total FA not FFA; these total FA values can only be used to estimate FFA. Thus, there is a critical need for an assay for free fatty acids (FFA) in any aqueous solution including plasma, serum and blood.

SUMMARY OF THE INVENTION

The invention described herein allows direct, continuous, and accurate measurement of free fatty acid (FFA), or other hydrophobic molecules for which a specific-binding protein exists or can be found, in a single reaction step followed by a detection step. The method uses a probe which is a fluorescently modified specific-binding protein for the analyte that undergoes a shift in emission wavelength upon binding to the analyte. In the exemplary embodiment, the probe, fluorescently modified free fatty acid binding protein (FABP), undergoes a change in fluorescence upon binding FFA, so that the ratio of emission intensities provides a direct measure of the FFA.

This invention is embodied, in the exemplary embodiment, in a method for determining free fatty acids comprising the steps of mixing a solution suspected of containing free fatty acid with a reagent comprising a fluorescently modified fatty acid binding protein, detecting a change in fluorescence of the fluorescently modified fatty acid binding protein, and relating said change in fluorescence to the amount of free fatty acid in the solution. The change in fluorescence may be qualitative, e.g. a shift in wavelength, or quantitative, e.g. an increase or decrease in intensity upon binding.

With an appropriate fluorescent moiety, the method can be used with whole blood, thereby eliminating the need to separate blood into plasma and cellular components.

Figure 6A:
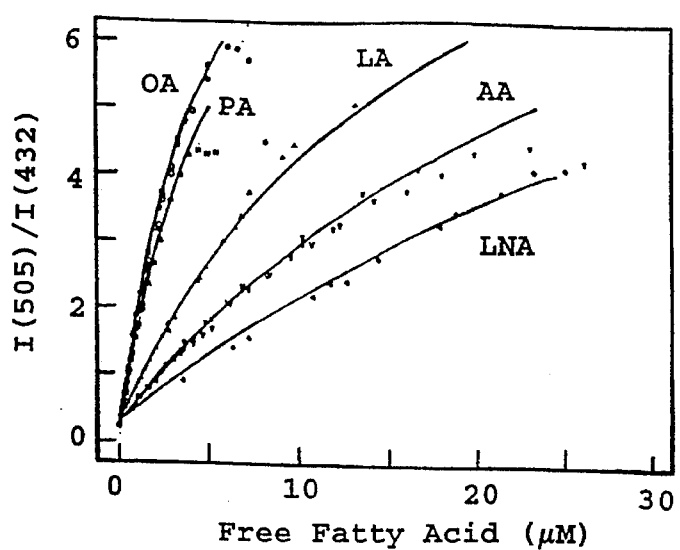
FIGS. 6A, 6B and 6C depict data showing the ADIFAB dose response to FFA and FFA aggregate formation. FIGS.
Figure 6B:
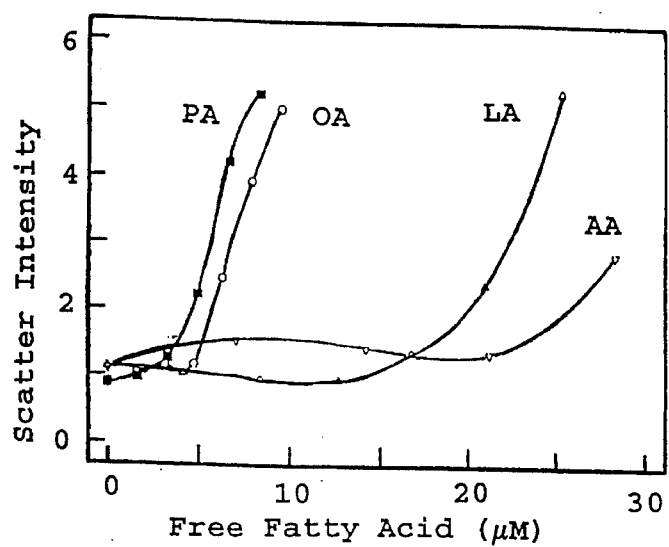
Figure 6C:
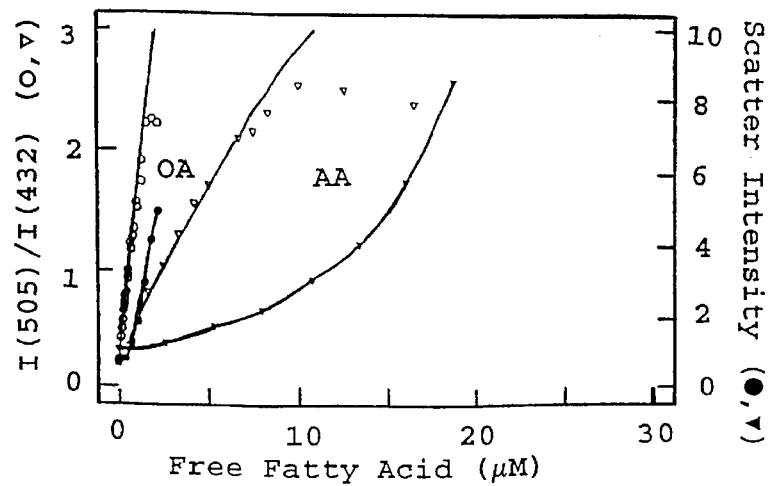

6A, 6B and 6C, respectively, depict the effect of the addition of FFA to ADIFAB, specifically depicting quenching of 432 nm and enhancement at 505 nm (FIG. 6A), light scattering (FIG. 6B), and reduction in the CMCs of Na oleate and arachidonate (FIG. 6C).

Figure 7:
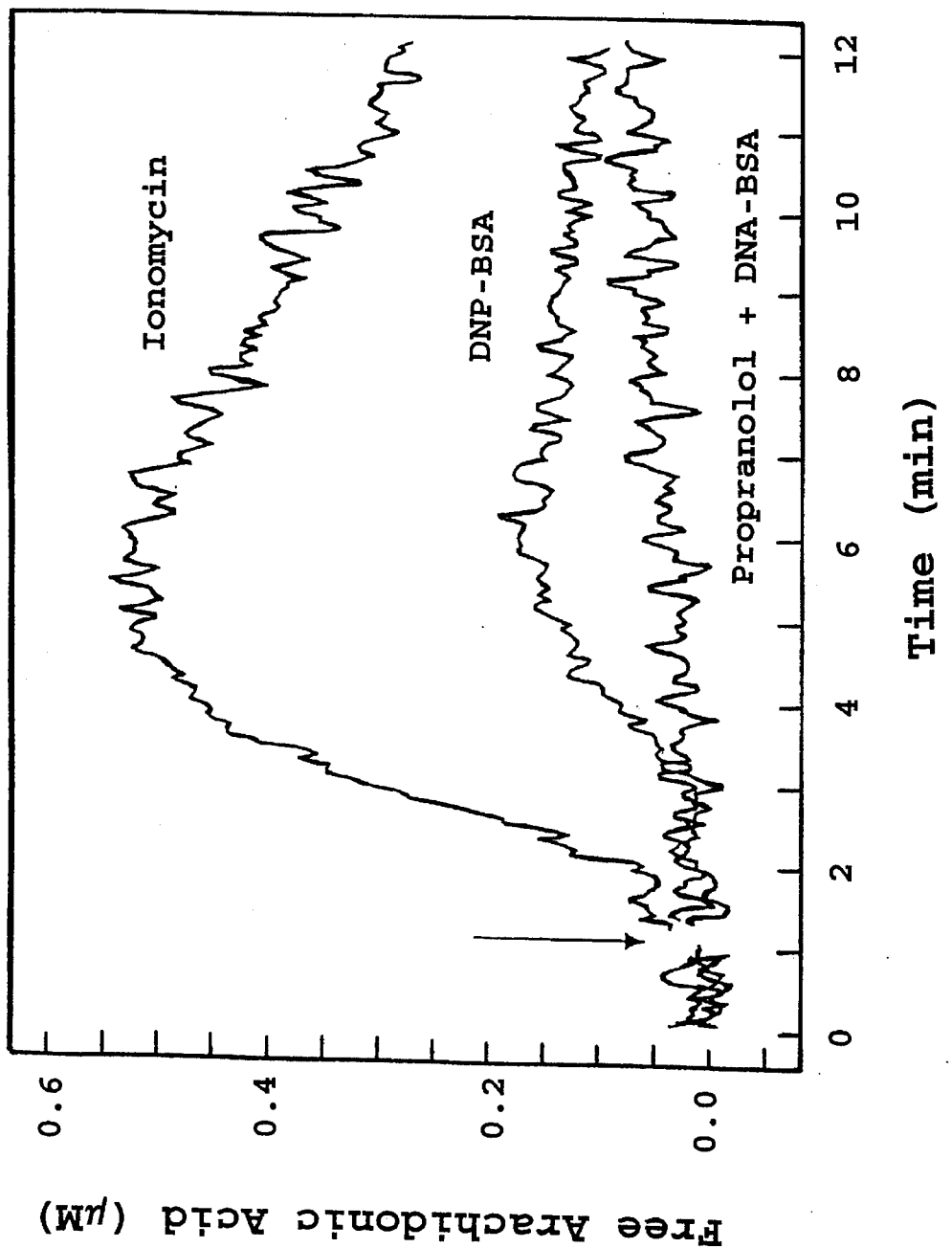

FIG. 7 depicts data showing the release of arachidonic acid as a function of time from red bloodlymphoctyes grown and treated with DNP specific IgE and suspended in aqueous buffer.

DESCRIPTION OF THE PREFERRED EMBODIMENTS

The assay of this invention involves the single determination of the fluorescence intensity of fluorescent FABP added to whole blood, serum or any aqueous solutions. Moreover, this method directly determines the concentration of unbound free fatty acids (FFA), the physiologically relevant form of the molecule. If so desired, then the total FA concentration could be calculated from the measured FFA and albumin concentrations.

Principles and exemplary methods for constructing probes as described and defined herein and methods for determining FFA levels are described in detail below. Using these principles fourteen different fluorescent-FABP derivatives have been constructed. This has been done using 3 different native FABPs (rat intestine (I-FABP), human adipocyte (A-FABP), and human heart (H-FABP)) plus 4 site-specific mutants of two of these (I-FABP, (Thr83_Cys83, Thr81_Cys81, Lys27_Cys27 and H-FABP, Thr27_Lys27), and these proteins have been derivatized with 4 different fluorophores (acrylodan, danzyl aziridine, 4-[N-[(2-iodoacetoxy)ethyl]-N-methylamino]-7-nitrobenz-2-oxa 1,3-diazole ester (IANBDE), 4-[N-[(2-iodoacetoxy)ethyl]-N-methylamino]-7-nitrobenz-2-oxa-1,3-diazole
these derivatives can serve as FFA probes, to some degree. To date, however, ADIFAB remains the one that has optimal properties for current applications. Obviously, by occupying, partially, the binding site with a fluorophore, FA must compete for its site and therefore the FA binding constant for the FABP may be altered from the native protein. This is indeed the case for ADIFAB for which the Kd is about 10 fold greater than for the native protein. So long as FA can bind, however, the derivatized molecule can still function as a FFA probe and so long as the probe's dynamic range is sufficient (as it is for ADIFAB, IANBDE and IANBDA) then FFA levels over a wide range, including those that are physiologic, can be measured.

Figure 1:
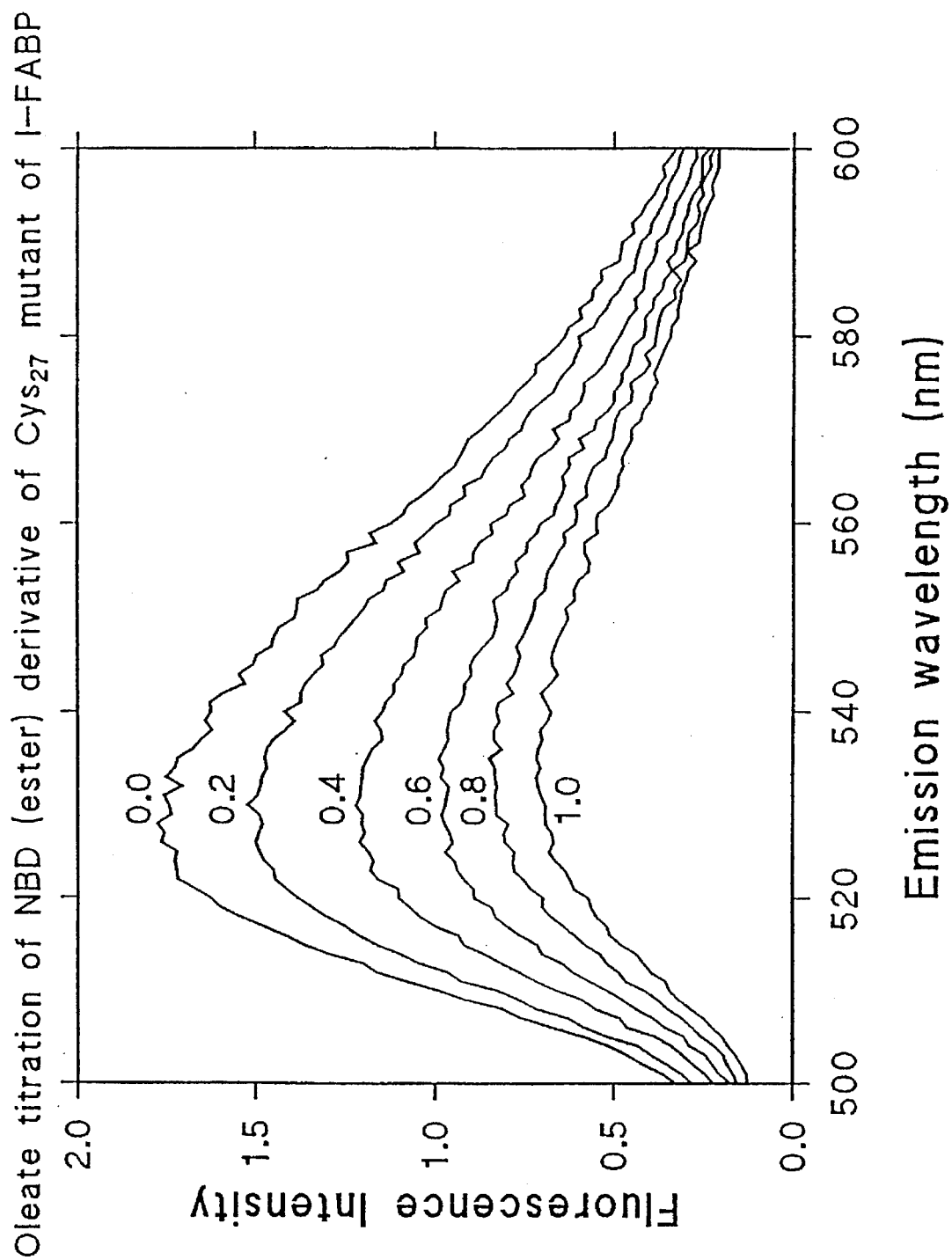
FIG. 1 is a graphical depiction of measured fluoresence intensity in the 500 to 600 nm wavelength region resulting from the titration of different levels of oleic acid with NBD (Ester) derivative of Cys27 mutant of rat intestinal fatty acid binding protein (I-FABP).
Figure 2:
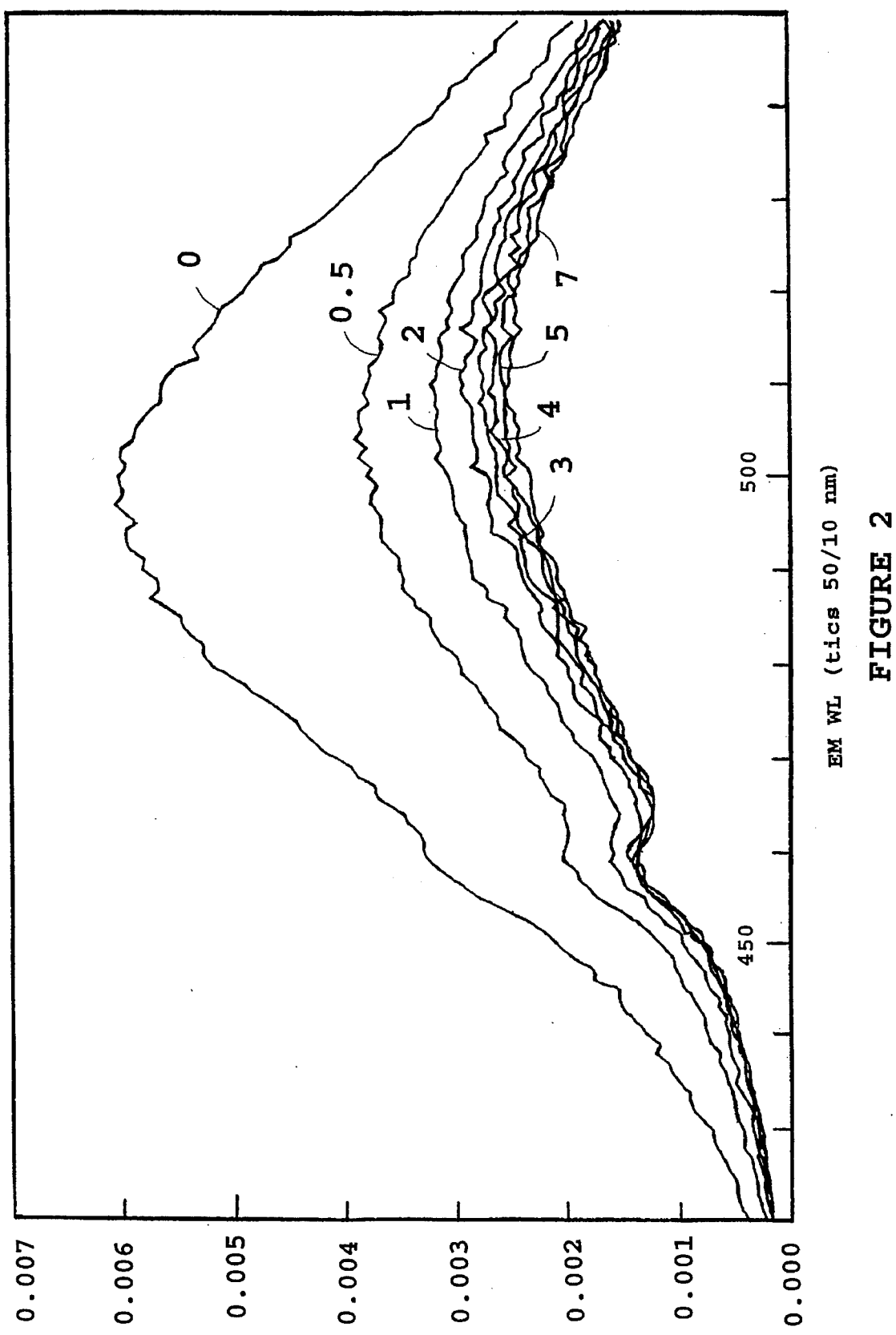
FIG. 2 is a graphical depiction of measured fluoresence intensity in the 420 to 550 nm wavelength region resulting from the titration of different levels of oleic acid with a danzyl aziridine derivative of Cys27 mutant of rat intestinal fatty acid binding protein (I-FABP).

In addition to ADIFAB (acrylodan to Lys27 on I-FABP), Lys27 on I-FABP with danzyl aziridine has been derivatized and this probe exhibits an increase in 450 nm fluorescence upon FA binding. The Cys27 mutant of I-FABP (Lys27 to Cys27) with acrylodan, IANBDE and IANBDA have also been labeled using the technique described. It was found that for the acrylodan derivative, the same general behavior as ADIFAB but instead of fluorescing at 432 nm, the apo form emits at 480 nm and therefore the relative change upon FA binding is smaller than for ADIFAB as graphically depicted in FIG. 1. This is the behavior predicted from the construction principles set forth herein, and reflects the shorter tethering arm to Cys27 as compared to Lys27 which prevents the deeper insertion into the binding site that is observed in the Lys27 derivative. Of the two nitrobenzofuran (nitrobenzoxadiazole, NBD) derivatives the IANBDE derivative is among the most sensitive, exhibiting with 1 mM oleate a 60% reduction in intensity at 550 nm with relatively little shift in emission wave length, as depicted in FIG. 2. The fluorescent label on I-FABP at Cys81 or Cys83 is unresponsive to FA binding, as expected since positions 81 and 83 are virtually on the opposite side of the protein from the portal region. Native A-FABP which contains two cysteines, was labeled with acrylodan and with the N-[7-(4-nitrobenzo-2-oxa-1,3-diazol) (NBD) moieties and these probes were found to be only poorly responsive, as expected since one of the cysteines lies within the binding site and therefore prevents FA binding. The Lys27 mutant of H-FABP was also labeled with acrylodan and as expected this is a highly responsive probe. Thus, those skilled in the art can with considerable confidence predict whether protein modifications and/or choice of label will result in a FFA responsive probe.

A reagent is prepared by any of the techniques described below, or other techniques that can, using the guidance of this disclosure, be adapted to such preparation. The reagent comprises a protein that has been labeled with a fluorescent moiety that, when so labeled, specifically binds to free fatty acid and which exhibits one fluorescence when unbound and a different fluorescence when bound to free fatty acid, the fluorescence difference being photometrically detectable. Native FA specific binding protein (FABP) or mutated FABP can be used to provide FA reactive binding sites. Exemplary fluorescent labels are described below. The nature of the fluorescent label is not critical, however. It need only be capable of being attached to the specific binding protein and, when attached, fluoresce detectably differently when the protein is bound as compared with unbound fluorescence. The mode of detection is also not critical. In other words, the label and the mode of detection are not critical limiting factors in this invention.

The fluorescence difference between a reagent wherein substantially all or a known portion of the reagent is unbound and the resulting mixture from the preceding mixing step is detected or measured. The change in fluorescence is related to the amount of free fatty acid in the solution. This may be a qualitative relationship, i.e., FFA present or not present above some threshold level, but most often the fluorescence change is related quantitatively once the FA binding constant (Kd) has been determined, as described below using equation (3), to the concentration of FFA. Examples of this, and the other steps, are given below.

EXEMPLARY METHODS AND MATERIALS

A clone carrying the I-FABP CDNA was identified in a neonatal rat intestinal CDNA library (STRATAGENE) using an oligonucleotide probe corresponding to the published sequence of IFABP. The cloned 640 base pair CDNA had a nucleotide sequence (determined by the dideoxy chain termination method, Bankier, A. T., & Barrell, B. G. (1983) Techniques in nucleic acid biochemistry. Vol. 35, Flavell, R. A., ed., Elsevier Scientific Publishers, Dublin, Ireland pp. 1–34) in agreement with the published sequence. This cDNA was inserted into the expression vector pET 11 a and the protein was expressed in the E. coil strain BL21 (both PET11A and BL21 were purchased from NOVAGEN). The I-FABP protein was purified from cell lysates essentially by the method of Lowe et. al. (Lowe, .J. B., Sacchettini, J. C., Laposata, M., & McQuillan, J. J. G., J. I. (1987) J. Biol. Chem. 262, 5931–5937.) Yield of purified protein was approximately 80mg per liter of E. coil culture.

Recombinant I-FABP was fluorescently labeled with 6-acryloyl-2dimethylaminonaphthalene (Acrylodan) (Prendergast, F., Meyer, M., Carlson, G., Iida, S., & Potter, J. (1983) J. Biol. Chem. 258, 7541–7544.). Acrylodan (Molecular Probes) was used to label I-FABP because its sensitivity to the polarity of its environment was expected to make it particularly responsive to the interaction of FFA and I-FABP and because Acrylodan is capable of covalent modification of protein amino acid residues. In preliminary studies this nominally thiol reactive reagent was used to derivatize an engineered cysteine-containing mutant of recombinant I-FABP, designated FAD508, since native I-FABP contains no cysteine residue (Kleinfeld, A. M., Ogata, R. T., & Richieri, G. V. (1991) Biophys. J. 59, 637a.) Later investigation showed that recombinant native I-FABP can be Acrylodan derivatized with high efficiency and most subsequent studies have been done with the Acrylodan derivatized recombinant native protein, designated ADIFAB. To carry out the reaction, I-FABP was first delipidated by Lipidex 5000 (Packard Instruments) chromatography (Glatz, J., & Veerkamp, J. (1983) Anal. Blochem. 132, 89–95.) Acrylodan, from a 20 mM stock solution in dimethylformamide, was then added, at 4mM, over approximately 10 minutes, to a 1 mg/ml solution of delipidated I-FABP in a buffer consisting of 10 Mm Boric acid and 150 Mm KCl at pH 9. The final Acrylodan/I-FABP molar ratio in the reaction mixture was 3:1 and the total Acrylodan concentration was 200mM. The reaction was monitored by the increase in Acrylodan fluorescence (emission at 432 nm) and allowed to proceed until no further increase could be detected, about 48 hours at 4° C. Unreacted Acrylodan was separated from the reaction product by exchange with Lipidex at 37° C. The resulting product exhibited a stoichiometry of about 1 Acrylodan per protein as determined from the ratio of protein absorbance at 280 nm (i=13400 (cm M)-I) to Acrylodan absorbance at 370 nm (f=10600 (cm M)-I). The site of Acrylodan labeling of the product to Lys27, (designated ADIFAB for AcryloDan labeled Intestinal Fatty Acid Binding protein), was determined by analysis of tryptic fragments of ADIFAB using a C 18 reverse phase HPLC with a water/acetonitrile solvent system. (ADIFAB is available from Molecular Probes, Eugene, Or.) Whole protein and proteolytic fragments were identified by amino acid analysis carried out by the protein analysis facility of the Research Institute of Scripps Clinic.

In most of the studies FFA was added to ADIFAB, in a buffer (A) consisting of 10 Mm HEPES, 150 Mm NaCl, 5 mM KCl, and 1 mM NaHPO4 at pH 7.4, as the sodium salt of the fatty acid. FFA was added as the Na salt rather than the acid in organic solvents because ADIFAB fluorescence was found to be sensitive to even small amounts (<0.1% by volume) of organic solvents such as ethanol or DMSO. FA bind to most surfaces and values of the total FA concentration ([FAT]) were corrected for FA binding to cuvette and container walls. This binding was determined using trace amounts of 14° C labeled FA and, separately, ADIFAB florescence to determine the degree of FA loss upon transfer from one container to another. The degree of FA binding to surfaces was found to be inversely proportional to the aqueous phase solubility of the FFA and amounted to between 8 and 21% of added FFA. To minimize FA binding to surfaces, the monomer concentrations of stock solutions of the Na salts were maintained at pH > 9.0 in water, and were warmed to > 37° C. just prior to use. The polyunsaturated forms of the FA are subject to oxidation and it was observed that dissociation constants for binding to ADIFAB (Kd) were considerably greater for the oxidized FA. Care was taken to reduce the exposure of the FA salts to oxygen (all handling was carried out under Argon) and to store them at −20° C.

The concentrations of FA in the aqueous phase (FFA) and FA bound to ADIFAB ($[FA_b]$) were determined from the ratio of fluorescence emission intensities at 432 and 505 nm (R). The values FFA and $[FA_b]$ were related to the ratio of intensities essentially by the method of Grynkiewicz et. al. (Grynkiewicz, G., Poenie, M., & Tsien, R. Y. (1985) J. Biol. Chem. 260, 3440–3450), according to which:

$$FFA = K_d Q (f_r / 1 - f_r) \quad (1)$$

and $$[FA_b] = [ADIFAB_{total}] Q(f_r)/(1 - f_r + FRQ) \quad F_R \geq R/\geq R_{max} \geq R = R = R_O \geq R_{max} - R_o, Q = 1_F(432)/I_b(432), I_f(432) \text{ and } I_b(432)$$

are the ADIFAB intensities with zero and saturating concentrations of FFA, $R_o$ is the intensity ratio in the absence of FFA and $R_{max}$ is the value when ADIFAB is saturated.

Because of the limiting solubility of long chain FA in aqueous solution $R_{max}$ and Q cannot. in general, be determined directly. To determine $R_{max}$ and Q, ADIFAB was titrated with lauric acid (12:0) whose high CMC allowed maximum R values (~10–11) to be measured that were considerably greater than with longer chain FA. From this titration a linear correlation was found between Q and R. Using Q, R pairs predicted by this relationship, a two parameter ($K_d$ and $R_{max}$) least squares analysis of each FA was done using the equation for equilibrium binding;

$$1/[FA_b] = (K_d/[ADIFAB])/FFA + 1/[ADIFAB] \quad (3)$$

Optimal Q and $R_{max}$ values obtained in this analysis were in the range 17–22 and 10 and 13, respectively, with average values of 19.5 and 11.5. Final Kd values for each FA were then determined by least squares analysis of equation (3) with Q and $R_{max}$ fixed at 19.5 and 11.5, respectively.

Fluorescence measurements to monitor Acrylodan fluorescence in various solvents, to monitor adduct formation, and to obtain complete spectra were carried out using an SLM 8000C fluorometer. Measurements of the 505/432 intensity ratios (R values) used to monitor the FFA titrations of ADIFAB were done with either the SLM 8000C or a Perkin-Elmer MPF-2A fluorometer.

FABP are small (14–15 Kda) proteins widely distributed in many cells, especially intestinal epithelium, liver, adipose and cardiac tissue. FABP specifically bind long chain FA. The intestinal form of the protein has a single FFA binding site. The specificity of the binding is fairly pronounced; Kd for FFA with chain lengths <14 carbons is quite large (low level of binding), and somewhat different proteins are required for binding sterols, retinol and other small hydrophobic molecules. The interference of other hydrophobic molecules is not usually a significant factor because of the above-described discrimination of the FABP and because the relative aqueous (of blood plasma) phase concentration of potential competitor molecules is negligible in comparison with long chain FFA.

The ability of FABP to discriminate in favor of long chain FFA has its origins in the unusual properties of the binding site. The x-ray structure of the I-FABP has recently been solved to about 2.5Å, and the solution was obtained with palmitic acid complexed with the protein, Sacchettini, J. C., Gordon, J. I. and Banaszek, L. J. J. Biolo Chem. 63:581 5, 1988. This structure shows that the FFA is bound in a "'clam shell"-like pocket formed by twelve strands of beta sheets. The FFA is bound so that its acyl chain is bent at the middle position (between carbon 6 and 8), suggesting a fairly constrained conformation. A fluorescence spectroscopic Study of the liver form of this protein (expected to have a structure similar to I-FABP) and its interaction with anthroyloxy-FA, Storch, J., Bass, N. M. and Kleinreid, A. M. J. Biol. Chem.264:8708, 1989, using a series of long chain FA in which an anthroyloxy moiety is ester linked to one of eight different positions along the acyl chain (n-AOFA), directly demonstrated that the FA is highly constrained at the 6–9 positions.

In early work, cloning was carried out using a cDNA library from neo-natal rat intestine purchased from STRATAGENE ( 11099 North Torrey Pines Rd., La Jolla, CA 92037). The library is carried by the LAMBDA ZAP II vector and was used with the E. coil host strain XL 1Blue which is supplied with the library. The recombinant clone was identified with an oligonucleotide probe based upon the published sequence of the I-FABP DNA (Lowe, J. B., Sacchettini, J. C., Laposata, M., McQuillan, J. J. and Gordon, J. I. J. Biol. Chem. 262:5931, 1987) and sequencing of 5 and 3 regions was used to verify the identity and completeness of the gene. The amino acid sequence of this clone was found to be identical to that described earlier by Lowe et. al. (1987, J. Biol. Chem. 262:5931 ). The I-FABP gene was removed from the lambda Zap vector and inserted into a PET expression vector (PET11 D) purchased from Novagen and the protein was expressed using the E. coil strains (BL2 1) also from Novagen (Madison, WI, USA). I-FABP is isolated from E. coil and purified as described, Lowe, J. B., Sacchettini, J. C., Laposata, M., McQuillan, J. J. and Gordon, J. I. J. Biol. Chem. 262:5931, 1987. In this procedure cells, after a 3-hour culture, are lysed, centrifuged to remove cell debris and the pellet frozen at -70oC. The frozen pellet was allowed to thaw in the presence of a lysing buffer composed of 50mM Tris, 0.5mM EDTA, 0.5mM PMSF, 0.1% Triton X100, at pH 8.0. This was centrifuged at 20,000 g. for 45 minutes and the pellet was discarded. The lysate was then subjected to two rounds (50% and 70%) of ammonium sulfate precipitation and the supernatant from the 70% material was desalted and concentrated using an Amicon ultrafiltration apparatus with a YM10 filter. The flitrate was then subjected to DEAE-Sephadex (A50), followed by Sephadex G-75 chromatography and the low molecular weight fractions were saved. This material gives a single band on 12% PAGE and an amino acid analysis of this material was consistent with the amino acid sequence of I-FABP. This procedure yields about 70 mg/1.0 liter fermentation of a single band running at about 14.6 Kda on SDS-PAGE. The addition of FFA (oleate, stearate, or palmitate) reduced the tryptophan fluorescence of the native protein by as much as 40%.

Site-directed mutagenesis was used to introduce a cysteine residue at positions 82 or 84, in place of the threonine residues that are normally at this position. Mutagenesis was carried out by annealing a synthetic primer with a single mismatched base to the above derived expression vector. The primer was extended and ligated in vitro, and the resulting heteroduplex was used to transfect the host strain. The transfected host was screened for the mutated DNA by hybridization with the mutating oligonucleotide. Mutated plasmid DNA was isolated, retransformed into the host strain, and its structure confirmed by sequencing the recombinant DNA in regions defined by probes flanking the mutated region. This modified protein was expressed in the same system and purified by the same methods as for the native protein. Typical yields of purified protein were approximately 50 mg/liter cell culture. The mutated I-FABP protein was fluorescently derivatized by inserting a fluorescent group (which reacts specifically with free SH groups) at the newly created cysteine residue. The cysteine residue was inserted at positions 82 (replacing a threonine residue) and/or at residue 84 (also a threonine residue) since both these positions face outward from the FFA binding pocket but are in close proximity to the tryptophan at position 83 (about 3.5Å lateral separation along the b strand and about 10Å vertical separation between the centers of the tryptophan and fluorescent residues). It was postulated, since the tryptophan fluorescence decreases upon FFA binding and the x-ray structure indicates that Trp83 specifically interacts at the FFA bend, that Trp83 may rotate into a lower dielectric environment which in turn will induce a change in the environment of residues 82 and 84. Thus, either the direct emission of the fluorescent group and/or the rate of resonance energy transfer between Trp83 and the fluorescent group was postulated to change. In a non-limiting prior specific example, the dansyl derivative ACRYLODAN® (6-acryloly-2dimethylamenonaphthalene) was used to modify the mutated FABP and this probe was designated FAD508.

Figure 3:
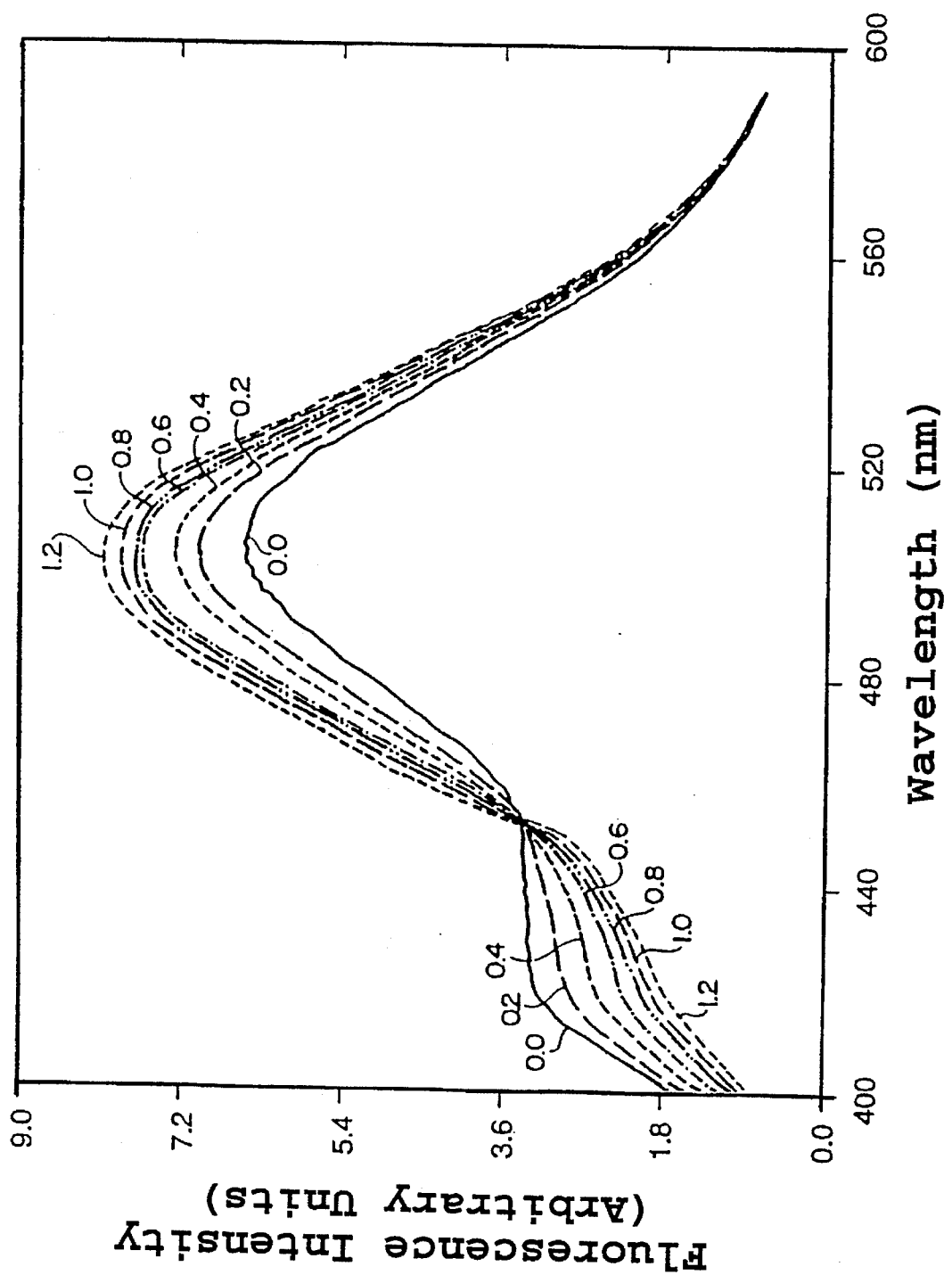
FIG. 3 depicts the fluorescence emission spectra of FAD 508 titrated with oleic acid. (FAD 508 is recombinant intestinal (I)FABP with Thr82-Cys82 mutation and which is derivatized with ACRYLODAN. )

Reference is made to FIG. 3 which depicts the fluorescence emission spectra of FAD508 titrated with oleic acid. The emission of IFABP, in which Thr-82 has been mutated to Cys-82 and this cysteine was derivatized with ACRYLODAN, is shown as a function of increasing concentrations of unbound oleic acid. The protein was dissolved at a concentration of 0.5mM in an aqueous buffer consisting of 50mM Tris, 150mM KCl, 0.5mM DDT, 0.02% Na Azide, pH 7.4. Oleic acid was added as a complex with small unilamellar vesicles of dimyristoylphosphatidylcholine (DMPC). The vesicle concentration was fixed at [DMPC] = 500mM, total oleic acid varied between 0 and 100 mM, and unbound oleic acid was determined using a partition coefficient of 70,000. The unbound oleic acid for each spectrum are indicated in FIG. 3. These spectra were obtained using an SLM4800 fluorometer in the ratio mode, with excitation wavelength = 400nm, excitation slits at 4nm and emission at 16nm.

Thus, addition of long chain FFA to this modified protein caused a monotonic spectral change with increasing FFA concentrations. These changes occurred in the same concentration range as those observed in the native protein and indicate that the mutagenesis and fluorescent modification did not abolish the FFA binding characteristics of the protein. These early results indicated that the ratio of fluorescence emissions at 430 and 497nm may provide a direct measure of the concentration of unbound FFA.

Figure 4:
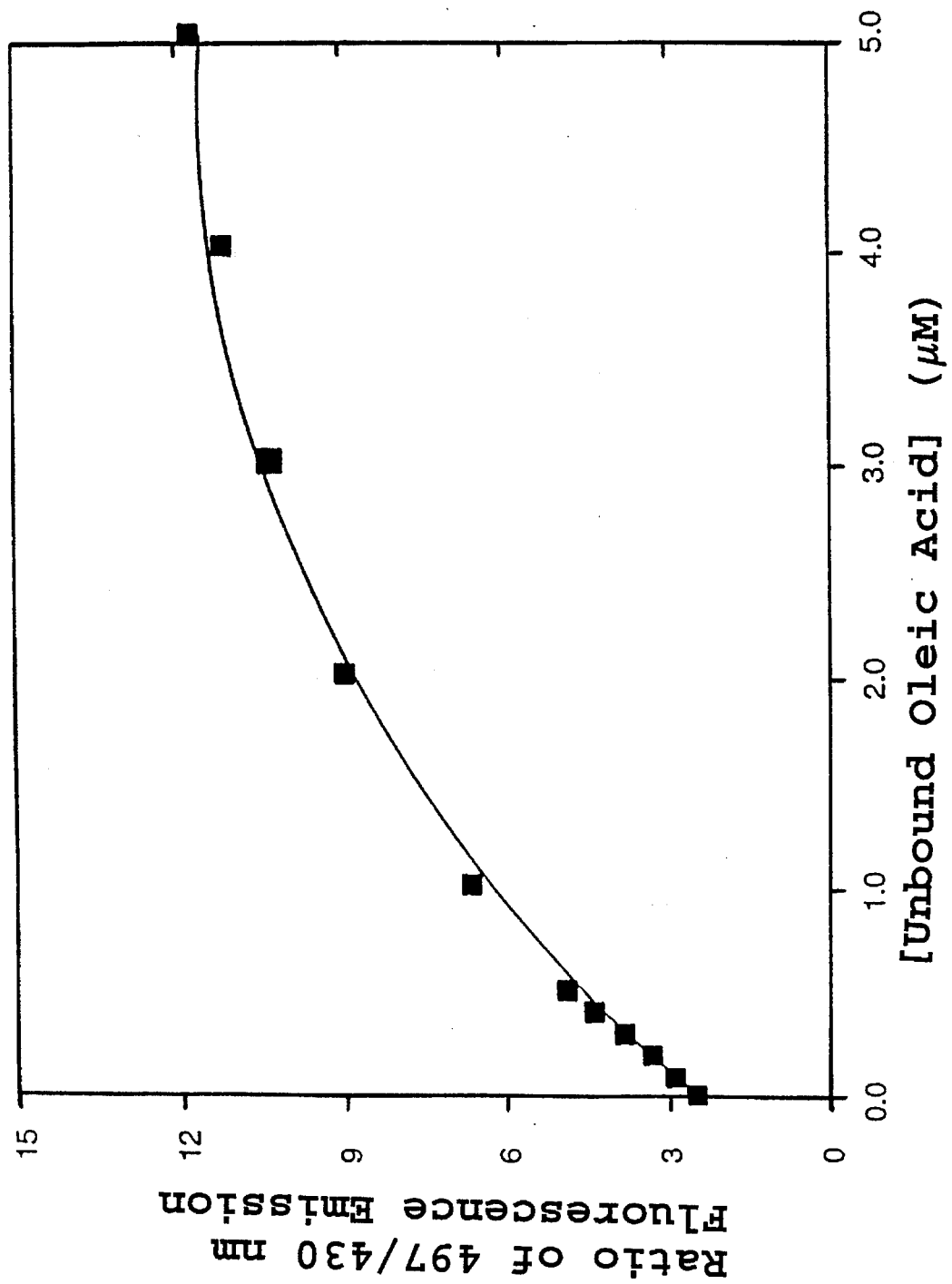
FIG. 4 depicts the ratio of 497nm to 430nm emission intensities for FAD 508 as a function of unbound oleic acid.

As shown in FIG. 4, the ratio of 497nm to 430nm emission intensities varies monotonically with increasing unbound FFA concentration. The zero FFA value is about 2.5 and the maximum value, at saturation (4mM oleic acid) is about 18.

Figure 5A:
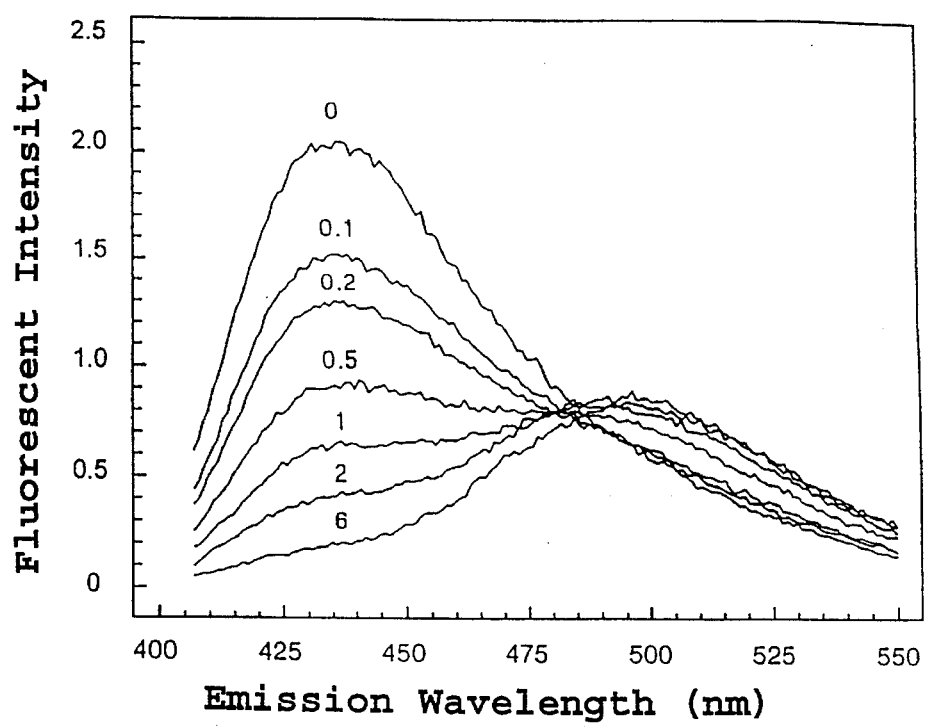
FIG. 5A depicts data showing the emission spectra of ADIFAB (ADIFAB is Acrylodan derivatized native IFABP) at excitation wavelengths of 386 nm.
Figure 5B:
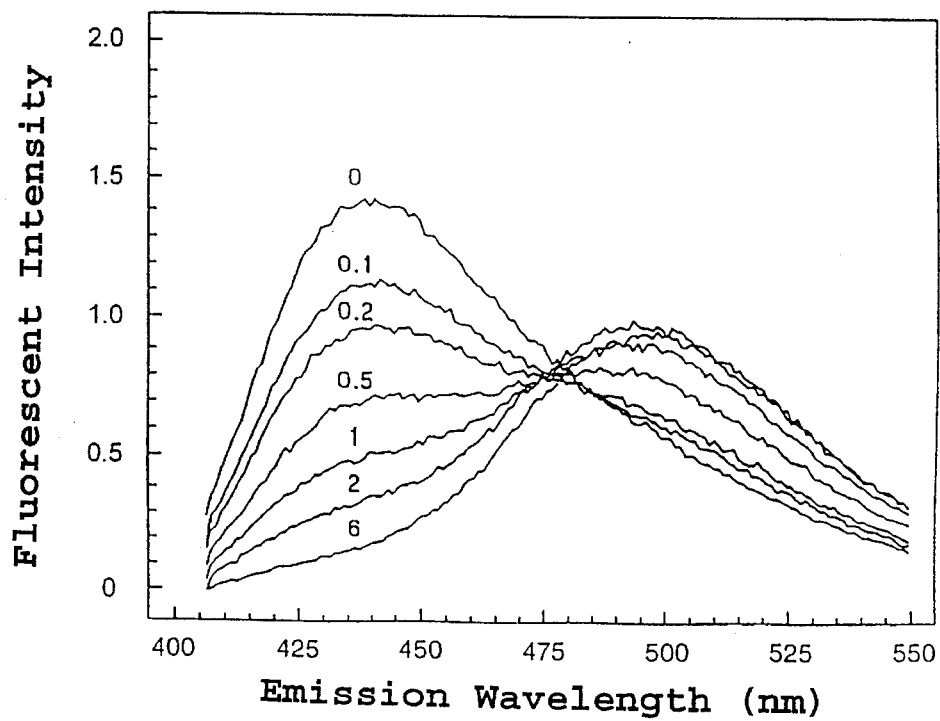
FIG. 5B depicts data showing the emission spectra of ADIFAB at excitation wavelengths of 400 nm.

The mutant protein derivatized with dansyl aziridine also showed an altered fluorescence response with added FFA and was considered advantageous when a shorter wavelength emitting probe is desired. A variety of fluorescent labels are available for use at various wavelengths Referring again to early results, ADIFAB (the acrylodan derivative at Lys27 of the native I-FABP) emission spectra were measured at excitation wavelengths of 386 nm and 400 nm respectively. These measurements were done by titrating the Na salt of oleic acid into 0.2mM ADIFAB in buffer A using an SLM 8000C fluorometer as described in Methods. Each spectrum is labeled with the concentration of added FFA in mM at A) 386 nm excitation and B) 400 nm excitation. FIGS. 5A and 5B show that the shape of the fluorescence emission spectrum of the FFA probe is extremely sensitive to FFA binding. Fluorescence emission from apo-ADIFAB is dominated by an emission peak at 432 nm, while in holo-ADIFAB fluorescence occurs at 505 nM. Several observations suggest that the FFA-induced spectral change is likely due to displacement of the Acrylodan moiety from the hydrophobic FA binding pocket into the aqueous environment. First, Acrylodan fluorescence in solvents of varying polarity indicate a continuous shift in emission from 430 nm in non-polar solvents to 540 nm in water. Second, it was found that the efficiency of Acrylodan labeling is much greater for apo as compared to holo I-FABP, suggesting that FFA blocks access to the reactive amino acid. Third, in the apo-protein the 505/432 ratio increases with excitation wavelength (FIG. 5B), suggesting that the Acrylodan moiety can sample two separate environments. In the apo-protein the predominant one lies within the hydrophobic FFA binding pocket of I-FABP where Acrylodan fluoresces at 432 nm and a minor one projects into the aqueous environment where Acrylodan fluoresces at 505 nm. Consistent with the excitation wavelength dependence of FIGS. 5A and 5B, it was found that the excitation maximum of a mercaptoethanol adduct of Acrylodan shifts to longer wavelengths in solvents of increasing polarity. Fourth, environmental changes resulting from Acrylodan displacement rather than a protein conformational change is consistent with x-ray crystallography, indicating virtually no difference in apo and holo forms of I-FABP (Sacchettini, J. C., Gordon, J. I., & ) Banaszak, L. J. (1989) Proc. Natl. Acad. Sci. USA 86, 7736–7740).

ADIFAB dose response to FFA and FFA aggregate formation was measured. The ratio of fluorescent intensities at emission wavelengths of 505/432 nm were measured as a function of added Na salts of several FFA. Resulting data are depicted graphically in FIGS. 6A, 6B and 6C. Conditions were similar to those used in FIG. 3 except that 100mM EGTA was used in obtaining the data depicted in FIGS. 6A and 6B, while the data depicted in FIG. 6C was obtained using 1 mM $CaCl_2$. Measured R values were used to determine FFA and [FFAb] using equations (1) and (2). The solid curves through the data of FIGS. 6A and 6C represent best fits of equation (3) obtained using a non-linear least squares algorithm. Aggregate formation was detected by measuring 90° light scattering from FFA in the buffer of FIG. 3 containing no added calcium and titrated with the Na salts of the FFA as described above, see FIG. 6B. The smoothed curves through the data, intended to guide-the-eye, indicate that aggregate formation, as detected by a sharp increase in light scattering, is approximately coincident with the maximum R value observed in the experiment related to FIG. 6A. FIG. 6C shows the effect of 1 mM calcium on the ADIFAB dose response curves and light scattering intensities for oleate and arachidonate. Each data point is an average of 10 separate measurements for which the standard deviations were less than 2%. (OA:O; PA:■; LA:△; AA:▽; LNA ◇).

Addition of FFA to ADIFAB results in quenching of 432 nm and enhancement at 505 nm with up to a 25-fold increase in the emission ratio (FIG. 6A). The 505/432 ratio therefore provides a sensitive measure of FA binding. The solid curve through the titration data of FIG. 6A represents a best fit analysis assuming equilibrium binding between aqueous FFA and a single FA binding site per ADIFAB molecule. This analysis provides an excellent description of FA binding to ADIFAB for all data below the critical micelle concentration (CMC). Equilibrium constants for the physiologically important long chain FFA were determined from this analysis (FIG. 6) and these values are listed in the Table I. The results show that the two most abundant FA, palmirate and oleate have the smallest Kds, the values for palmirate, linoleate, arachidonate, and linolenate are, respectively, about 1.1, 3.5, 5.8, and 8.9 fold greater than oleate.

The maximum ADIFAB fluorescence ratio occurs at concentrations representing .FA aggregate formation, rather than saturation of ADIFAB binding. These maximum concentrations probably correspond to the CMC of the FA. Aggregate formation was demonstrated by the abrupt increase in light scattering at these concentrations, as demonstrated in FIG. 6B. These results indicate that the fluorescence ratio change observed below the CMC is most likely due to the interaction between aqueous phase monomers of FA and the ADIFAB probe.

The aggregate state of FA is known to be particularly sensitive to the presence of calcium (Yamaguchi, T., Kaneda, M., & Kakinuma, K. (1986) Biochem. Biophys. Acta 861,440–446; Small, D. M. (1986) Plenum Press, New York). ADIFAB fluorescence and light scattering were measured in 1 mM Ca, about the level found in extra cellular fluid, as a function of FFA addition.-As FIG. 6C shows, there is a large, approximately 6-fold, reduction in the CMCs of Na oleate and arachidonate, as determined from the decrease in the ADIFAB titration maximum and the increase in light scattering intensity. Similar behavior was exhibited by saturated as well as other cis-unsaturated FA. These results indicate that monomer concentrations of the most abundant FA (palmitate and oleate) will not exceed 1–3 mM in extracellular fluid or plasma, but might achieve higher values in the intracellular environment where $[Ca^{2+}]$ is generally less than 1 mM (Tsien, R. Y., & Poenie, M. (1986) Trends Blochem. Sci. Sci. 11,450–455). Although calcium ions have a significant effect on the aggregate state of the FA, little or no effect was observed on Kd values, as determined by a fit of equation (3) to R values obtained at FFA concentrations below the CMC. For example, Kd values for oleate and arachidonate in 1 mM calcium were found to be 0.31 and 1.67 mM, respectively.

ADIFAB is highly specific for long chain FA. As discussed above the physiologically important long chain FA have Kd values in the range < 0.2 to 2.5mM, while binding of shorter chain FA such as laurate (12:0), although detectable, is considerably weaker with a Kd > 200 mM. The interaction between ADIFAB and a variety of molecules that are either formed in association with FA or coexist with FA in plasma and might therefore compete with FA for binding to ADI FAB were examined. The following molecules were investigated up to the maximum concentrations indicated in parenthesis; lysolecithin (100mM), sphingosine (1 00mM), bilirubin (50mM), leukotriene C4 (32mM), (5S)-5-Hydroxy-6,8, 11,14-eicasatetaenoic acid (5-HETE) (10mM), and prostaglandin D2 (5mM). Although these concentrations exceed their physiological values none of these molecules, either themselves cause a change in ADI-FAB fluorescence, nor do they displace oleic acid binding to ADIFAB. (Since these molecules are water insoluble they were added to ADIFAB from ethanol, at 0.1% by volume, which itself causes an Ro increase by about 12% but has no effect on the Kd for oleate binding. )

The results of this study, both original results and current results, demonstrate that I-FABP derivatized with Acrylodan (ADIFAB) is a highly specific and extremely sensitive probe of FFA, the aqueous phase monomers of long chain fatty acids. ADIFAB is sensitive to FFA levels, depending upon the FA, between 1 nM for oleic acid to about 20 nM for linolenic acid, concentrations that are expected to be significantly lower than physiological levels (Ashbrook, J. D., Spector, A. A., Santos, E. C., & Fletcher, J. E. (1975) J. Biol. Chem. 250, 2233–2338).

exposed position.

TABLE I

| FA-ADIFAB Dissociation Constants FFA | | | | |
|---|---|---|---|---|
| PALMITATE | OLEATE | LINOLEATE | ARACHIDONATE | LINOLENATE |
| $K_d$* 0.32 ± 0.01 | 0.28 ± 0.01 | 0.97 ± 0.02 | 1.63 ± 0.03 | 2.5 ± 0.1 |

*Kd values (mM) were determined from the binding measurements of FIG. 6A, using the methods described in the text. Uncertainties in these values were determined from the combined 505/432 value uncertainties (±2%) and the uncertainties in FFA concentration (±4%). The values shown in parenthesis are values normalized to the corresponding value for oleate.

DISCUSSION

The sensitivity, selectivity, and convenience with which ADIFAB allows FFA to be determined will make it useful in a variety of applications. ADIFAB is being used currently to determine serum levels of FFA and to monitor phospholipase activity in vitro. In addition, the ratio nature of its response will allow ADIFAB to be used in studies of extra and intracellular release of FFA by fluorescence ratio imaging microscopy, and such studies are also in progress.

As illustrated by the examples, it is not difficult for one skilled in the art of protein chemistry following the teachings of this invention to construct a new fluorescent probe of FFA based upon the methods of this invention. The essence of these methods is that an environmentally sensitive fluorescent group, attached to an appropriate amino acid on a fatty acid binding protein (FABP), will undergo a shift in position, and therefore fluorescence, when an empty FABP binds a fatty acid (FA). This shift in fluorescence can be used to determine the concentration of FFA.

Although, in an arbitrary FABP, one cannot predict, a priori, exactly which residue is best to label or which fluorophore will be optimal, straight forward and limited experimentation will reveal the correct choices. The choice of which amino acid position should be labeled with a fluorophore is dictated by a) the structure of the FABP family of proteins is, except for certain discrete locations, unchanged upon binding a fatty acid, b) there is only a single FA binding site in these proteins, and c) the location of this site is known from x-ray diffraction to be buried within the protein (5). In order for the fluorescent group to exhibit a change in fluorescence its position must change upon binding of a FA to the fluorescently labeled FABP. Thus, the fluorescent group must either label one of the discrete positions known from x-ray diffraction studies to change and/or it must label a residue position which allows the fluorophore to partially occupy the FA binding site. The acrylodonated intestinal fatty acid binding protein (ADI-FAB) and the other probes that have been constructed involve residue positions that allow the fluorescent label to partially occupy the FA binding site and involve residues that change positions upon FA binding (1). Thus, one end of the fluorophore is tethered to a (covalently modified) amino acid while the other end occupies, to varying degrees, the FA binding site. Upon binding to the labeled FABP, the FA displaces the fluorescent group from the binding site. The fluorescence (intensity and/or emission wave length) of the fluorophore when it is in the binding site reflects the low polarity environment and highly restricted nature of this site. Upon displacement from this site, by virtue of the FA binding, the fluorophore's fluorescence reflects the generally greater polarity and lower constraints in its now more exposed position.

Since the FA binding site is buried within the FABP, amino acid positions that are candidates for labeling must be located in regions of the protein from which the derivatized fluorophore can extend into the binding site. These regions are principally the amino acid positions that line the "portal" region of the protein (Sacchettini, J. C., J. I. Gordon and L. J. Banaszak,. (1989). J. Mol Biol. 208:327. This region forms the structure through which it is believed fatty acids must pass in order to access the binding site that is buried within the core of the protein. By attaching a fluorophore of the appropriate polarity, length, and shape to one of the residues within the portal region, the fluorophore can be tethered so that its distal end can insert through the portal into the binding site. The probes constructed to date have been attached to amino acids in the vicinity of positions 27 which is on a loop that forms part of the "portal" region. There is, however, no reason why other locations within the portal region might not be used, with appropriate fluorophores. One needs only to use a fairly hydrophobic fluorophore with a shape and size similar to the naphthalene derivatives used in the probes already constructed and it must have a sufficiently long chain or linkage portion so that it can extend from the label site into the binding site. The residues located both in the portal region and along a ridge that outlines the binding pocket but is on the outside facing surface of the protein and that exhibit orientational differences in the apo and holo protein structures are candidates for labeling. Any amino acid position can be labeled uniquely in those FABPs by site-directed mutagenesis, as demonstrated by the probes constructed to date.

The use of the probes described herein is the only way to measure free fatty acid concentrations, at least for the highly insoluble but physiologically dominant long-chain FA. Many reports exist in the literature that report measurements of "FFA". This is a common but incorrect usage of the term FFA. Free FA is the FA that is in true aqueous solutions. What these other methods actually measure is the total FA, the FA that is bound to proteins and cells plus the free FA. In all instances the FFA is an extremely small component of the total. For example, in human serum (where many studies erroneously report "FFA" values) the total FA concentration is about 0.5 mM whereas the free concentration is about 6 nM (Richieri and Kleinfeld data not shown). Thus, the FFA is about 1 part in 105 of the total! This free component, which is the biologically active portion of the total FA, can only be measured with ADIFAB or one of the other probes described above.

That this is a unique ability is becoming apparent to the scientific community at large, as shown by the studies published in first ranked peer reviewed journals since the filing of the original patent application and by the evident commercial success of ADIFAB. The studies which have been published since the filing of the original application leading to this patent are Richieri, G. V., R. T. Ogata, and A. M. Kleinfeld. 1992. A fluorescently labeled intestinal fatty acid binding protein: Interactions with fatty acids and its use in monitoring free fatty acids; J. Biol. Chem. 267:23495; Anel, A., G. V. Richieri, and A.M. Kleinfeld. 1993. Membrane partition of fatty acids and inhibition of T cell function. Biochemistry 32:530; Richieri, G. V., Ariel, and A. M. Kleinfeld. 1993. Interactions of long-chain fatty acids and albumin: Determination of free fatty acid levels using the fluorescent probe ADIFAB. Biochemistry 32: 574, 1993; Anel, A., and A. M. Kleinfeld. 1993. Tyrosine phosphorylation of a 100 KD protein is correlated with cytotoxic-T-lymphocyte function: Evidence from cis unsaturated fatty acid and phenylarsine oxide inhibition. J. Biol. Chem. 268: 17578, 1993). (See also BIOPROBES 17, Molecular Probes Inc.) BIOPROBES is a periodic publication of Molecular Probes Inc. that contains a short selection of about 100 probes used to inform the research community about new developments in fluorescent probes. Although the Molecular Probes catalog contains over 1800 probes, many of them synthesized by Molecular Probes itself, ADIFAB. described herein, has been extensively promoted by Molecular Probes. Of the four issues of the Bioprobes brochures that Molecular Probes has issued since ADIFAB was introduced, three of them described ADIFAB and two of these devoted sufficient space to exhibit a figure showing the ADIFAB spectral response to FFA.

There are numerous indications that alterations in FFA levels correlate with various states of health and disease. Heretofore, measurements of FFA levels could not be performed because there has been no method available. Elevated levels may be associated with various pathologies including ischemia, inflammation, diabetes, AIDS and cancer, monitoring blood levels could be used to directly and rapidly monitor the progress of treatment. The present invention is ideally suited to the measurement of FFA levels in any aqueous medium, including human serum. This invention is readily adaptable to measurements of the plasma levels of other hydrophobic molecules including, for example, free cholesterol, hormonal steroids such as estrogen, progesterone and testosterone, and retinoic acid. Using the teachings of the present invention, it now becomes a matter of routine experimentation using known fluorescent labeling techniques to label specific-binding proteins for free hydrophobic molecules. The fluorescent characteristics of a number of such fluorescently labeled specific-binding proteins when free and when bound to the analyte of interest are evaluated using well-known florescence methods. The fluorescently labeled specific-binding protein that provides the highest sensitivity will, as is well-known, generally be chosen as the reagent of choice. For example, specific-binding proteins are known for free retinol (Noy, N. et. al., Biochemistry 30:6380) (1991) and for cholesterol (Butko, P., et. al., Biochemistry 29:4070, 1990) the use of which as taught herein will provide methods within the invention for determining the level of these molecules.

The method of this invention provides a much faster and less expensive alternative to current methods for measuring the concentration of these molecules, if any method exists, The availability of the present method will permit the physician to have, on a regular basis at reasonable expense to the patient, very important information to aid in the diagnosis and treatment of diseases.

The exemplary method, fluorescence FABP, will also have wide applicability in studies of intra- and inter-cellular fatty acid transport, in models of inflammatory response, and in enzymatic assays such as those for various lipases. Industrially, the invention will be useful in detecting lipid degradation in food preparations.

INDUSTRIAL APPLICATION

The primary commercial application of this technology would be its inclusion in routine blood assay for FFA, lipids, steroids and other hydrophobic molecules in aqueous media, in assays involved in commercial production of certain food preparations, and in assays used in research in biochemistry and cell biology.

What is claimed is:

1. A method for determining the concentration of unbound free fatty acid in aqueous solution comprising the steps of: mixing an aqueous solution suspected of containing unbound free fatty acid with a reagent that consists essentially of a fatty acid binding protein that:
   (a) binds specifically to unbound free fatty acid in aqueous solution,
   (b) has been labeled with a fluorescent moiety, and
   (c) exhibits a first fluorescence
   when unbound in aqueous solution and a measurably different second fluorescence when bound to previously unbound free fatty acid in the aqueous solution; measuring the fluorescence difference that results from the binding of the fatty acid binding protein with the previously unbound free fatty acid; and obtaining the concentration of unbound free fatty acid in the aqueous solution from the measured fluorescence difference.

2. The method of claim 1 wherein the measuring step comprises determining the fluorescence at two wavelengths, and the concentration of unbound free fatty acid in the aqueous solution is obtained from the ratio of the fluorescences.

3. A method for determining the concentration of unbound free fatty acid in an aqueous solution comprising the steps of:
   mixing an aqueous solution containing unbound free fatty acid with a reagent that consists essentially of a fatty acid binding protein of about 14,000–15,000 daltons that:
   (a) binds specifically to unbound free fatty acid in the aqueous solution,
   (b) has been labeled with a fluorescent moiety, and
   (c) exhibits a first fluorescence when unbound in aqueous solution and a measurably different second fluorescence when bound to the previously unbound free fatty acid in the aqueous solution;
   measuring the fluorescence difference that results from the binding of the fatty acid binding protein with the previously unbound free fatty acid; and
   determining the concentration of unbound free fatty acid in the aqueous solution from the measured difference in the first and second fluorescences.

* * * * *

UNITED STATES PATENT AND TRADEMARK OFFICE
CERTIFICATE OF CORRECTION

PATENT NO. : 5,470,714                    Page 1 of 4

DATED : November 28, 1995

INVENTOR(S) : Alan M. Kleinfeld

It is certified that error appears in the above-indentified patent and that said Letters Patent is hereby corrected as shown below:

Column 2, line 24, change "Klausher" to --Klausner--

Column 2, line 42, change "that storch et al" to --that Storch et al--

Column 2, line 60, change "FFA have I O not been" to --FFA have not been--

Column 3, line 38, change "to quantirate the" to -to quantitate the--

Column 3, line 47, change "Anal. Blochem" to --Anal. Biochem--

Column 5, line 36, change "diazali these deruiatives" to --diazale amide (IANBDA) Most of these deruiatives--

Column 6, line 49, change "CDNA" to --$_c$DNA--

Column 6, line 50, change "CDNA" to --$_c$DNA--

Column 6, line 52, change "CDNA" to --$_c$DNA--

Column 6, line 59, change "E. coil" to --E. coli--

Column 6, line 65, change "E. coil" to --E. coli--

UNITED STATES PATENT AND TRADEMARK OFFICE
CERTIFICATE OF CORRECTION

PATENT NO. : 5,470,714

DATED : November 28, 1995

INVENTOR(S) : Alan M. Kleinfeld

It is certified that error appears in the above-indentified patent and that said Letters Patent is hereby corrected as shown below:

Column 7, line 19, change "Anal. Blochem." to --Anal. Biochem--

Column 7, line 24, change "Mm KCI" to --Mm KCl--

Column 7, line 34, change "(cm M)-1)" to --(cm M)-1)--

Column 7, line 34, change "370nm (F = 10600)" to --370nm (↑=10600)

Column 7, line 45, change "NaCI, 5mM KCI" to --NaCl, 5m MKCl--

Column 7, line 54, change "of 14°C labeled" to --of $^{14}$C-labeled--

Column 8, line 21, change "cannot. in general," to --cannot, in general--

Column 8, line 51, change "steroIs" to --sterols--

Column 8, line 63, change "Chem. 63:581" to --Chem. 263:5815--

Column 8, line 64, change ""Clam shell"" to --"Clam shell"--

Column 9, line 4, change "Kleinreid" to --Kleinfeld--

Column 9, line 14, change "E. coil" to --E. coli--

Column 9, line 19, change "5 and 3'" to --5' and 3'--

Column 9, line 23, change "E. coil" to --E. coli--

Column 9, line 28, change "E. coil" to --E. coli--

Column 9, line 54, change "prirmer" to --primer--

UNITED STATES PATENT AND TRADEMARK OFFICE
CERTIFICATE OF CORRECTION

PATENT NO. : 5,470,714

DATED : November 28, 1995

INVENTOR(S) : Alan M. Kleinfeld

It is certified that error appears in the above-indentified patent and that said Letters Patent is hereby corrected as shown below:

Column 10, line 24, change "IFABP" to --I-FABP--

Column 10, line 29, change "KCI" to --KCl--

Column 10, line 52, change "saliedtion (4mM" to --satuation (≈4mM--

Column 11, line 59, change "The-solid" to --The solid--

Column 12, line 1, change "palmirate and" to --Palmitate and--

Column 12, line 2, change "palmirate" to --palmitate,--

Column 12, line 20, change "in I mM Ca, about" to --in 1 mM $Ca_2$, about--

Column 12, line 21, change "-As Figure" to --As Figure--

Column 12, line 33, change "Trends Blochem." to --Trends Biochem.--

Column 14, line 32, change "within t.he portal" to --within the portal--

Column 15, line 8, change "G.V. Ariel" to --G.V. Anel--

UNITED STATES PATENT AND TRADEMARK OFFICE
CERTIFICATE OF CORRECTION

PATENT NO. : 5,470.714

DATED : November 28, 1995

INVENTOR(S) : Alan M. Kleinfeld

It is certified that error appears in the above-indentified patent and that said Letters Patent is hereby corrected as shown below:

Column 15, line 11 change "Biochemistry 32:574, 1993" to -- Biochemistry 32:7574, 1993--.

Signed and Sealed this

Eighth Day of October, 1996

Attest:

BRUCE LEHMAN

Attesting Officer

Commissioner of Patents and Trademarks